US010039627B2

(12) United States Patent
Chu (10) Patent No.: US 10,039,627 B2
(45) Date of Patent: Aug. 7, 2018

(54) MEDICAL DEVICE AND METHOD OF DELIVERING THE MEDICAL DEVICE

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 444 days.

(21) Appl. No.: 14/199,643

(22) Filed: Mar. 6, 2014

(65) Prior Publication Data

US 2014/0257028 A1     Sep. 11, 2014

Related U.S. Application Data

(60) Provisional application No. 61/776,411, filed on Mar. 11, 2013.

(51) Int. Cl.
*A61F 2/00* (2006.01)
*A61B 17/06* (2006.01)
*A61B 17/42* (2006.01)

(52) U.S. Cl.
CPC ...... *A61F 2/0045* (2013.01); *A61B 17/06109* (2013.01); *A61F 2/0063* (2013.01);
(Continued)

(58) Field of Classification Search
CPC .... A61F 2/0045; A61F 2/0022; A61F 2/0063; A61F 2/0036; A61B 2017/00805; A61B 17/00234
See application file for complete search history.

(56) References Cited

U.S. PATENT DOCUMENTS 6,575,897 B1    6/2003    Ory et al.
6,695,855 B1    2/2004    Gaston
(Continued)

FOREIGN PATENT DOCUMENTS

WO    2007106897 A2    9/2007
WO    2008048971 A2    4/2008
WO    2014164340 A1    10/2014

OTHER PUBLICATIONS

International Preliminary Report on Patentability for PCT Application No. PCT/US14/21983, dated Sep. 24, 2015, 9 pages.
(Continued)

*Primary Examiner* — Christine H Matthews
(74) *Attorney, Agent, or Firm* — Brake Hughes Bellermann LLP (57) ABSTRACT

In an embodiment, the invention discloses an implant that includes a first elongate member and a second elongate member formed monolithically with the first elongate member out of a single material and planar strip of material. The first elongate member includes a distal end portion and a proximal end portion. The second elongate member includes a first portion and a second portion. Further, each of the first portion of the second elongate member and the second portion of the second elongate member includes a proximal end portion and a distal end portion. The first portion and the second portion extend from the first elongate member. The distal end portion of the first elongate member is configured to be attached to or proximate a sacrum.

14 Claims, 9 Drawing Sheets

(52) U.S. Cl.
  CPC ..... *A61B 17/42* (2013.01); *A61B 2017/06052* (2013.01); *A61F 2230/006* (2013.01); *A61F 2250/0071* (2013.01)

(56) References Cited

U.S. PATENT DOCUMENTS

| | | |
|---|---|---|
| 7,985,173 B2 | 7/2011 | Jacquetin |
| 7,985,174 B2 | 7/2011 | Nicita |
| 7,998,055 B2 | 8/2011 | Siegel et al. |
| 8,057,382 B2 | 11/2011 | Thierfelder et al. |
| 8,109,867 B2 | 2/2012 | Rosenblatt |
| 8,262,557 B2 | 9/2012 | Chapman et al. |
| 8,460,171 B2 | 6/2013 | Von Pechmann et al. |
| 9,414,902 B2 | 8/2016 | Miller |
| 2002/0028980 A1 | 3/2002 | Thierfelder et al. |
| 2002/0095181 A1 | 7/2002 | Beyar |
| 2002/0183588 A1 | 12/2002 | Fierro |
| 2004/0087970 A1 | 5/2004 | Chu et al. |
| 2005/0101834 A1 | 5/2005 | Merade |
| 2007/0173864 A1 | 7/2007 | Chu |
| 2007/0270890 A1 | 11/2007 | Miller |
| 2007/0293717 A1 | 12/2007 | Kaleta et al. |
| 2008/0045894 A1 | 2/2008 | Perchik et al. |
| 2008/0119863 A1 | 5/2008 | Mellier |
| 2008/0146886 A1 | 6/2008 | Lucas |
| 2009/0171140 A1 | 7/2009 | Chu |
| 2009/0171142 A1 | 7/2009 | Chu |
| 2009/0171143 A1 | 7/2009 | Chu et al. |
| 2009/0216075 A1 | 8/2009 | Bell et al. |
| 2009/0326573 A1 | 12/2009 | Miller |
| 2010/0145140 A1 | 6/2010 | Chu |
| 2010/0191038 A1 | 7/2010 | Kubalak et al. |
| 2010/0280627 A1* | 11/2010 | Hanes, II ........... A61B 17/0218 623/23.72 |
| 2011/0105836 A1 | 5/2011 | Miller |
| 2011/0301407 A1* | 12/2011 | Deitch ............... A61B 17/0401 600/30 |
| 2012/0083807 A1 | 4/2012 | Mathisen et al. |
| 2012/0108894 A1 | 5/2012 | Young et al. |
| 2013/0006050 A1 | 1/2013 | Rane et al. |
| 2016/0331503 A1 | 11/2016 | Miller |

OTHER PUBLICATIONS

International Search Report and Written Opinion for PCT Application No. PCT/US14/21983, dated Jul. 3, 2014, 14 pages.

\* cited by examiner

MEDICAL DEVICE AND METHOD OF DELIVERING THE MEDICAL DEVICE

CROSS REFERENCE TO RELATED APPLICATION

This application is a Nonprovisional of, and claims priority to, U.S. Patent Application No. 61/776,411, filed on Mar. 11, 2013, entitled "MEDICAL DEVICE AND METHOD OF DELIVERING THE MEDICAL DEVICE", which is incorporated by reference herein in its entirety.

FIELD

The present invention generally relates to medical devices and procedures, and particularly, devices and methods configured to be delivered and placed in a patient's body for the treatment of pelvic organ prolapse.

DESCRIPTION OF THE RELATED ART

Pelvic organ prolapse is an abnormal descent or herniation of the pelvic organs. A prolapse may occur when muscles and tissues in the pelvic region become weak and can no longer hold the pelvic organs in place correctly.

Treatment for symptoms of the pelvic organ prolapse can include changes in diet, weight control, and lifestyle. Treatment may also include surgery, medication, and use of grafts to support the pelvic organs.

Sacrocolpopexy is one such surgical technique that may be used to repair pelvic organ prolapse. This can be performed using an open abdominal technique or with the use of minimally invasive surgery, such as laparoscopy or robotic-assisted surgery. The technique includes suspension of the apical portion of vagina (or sometimes the vaginal cuff after hysterectomy) using an implant such that the technique recreates the natural anatomic support.

In some cases, a Y-shaped implant may be used to treat vaginal vault prolapse during the sacrocolpopexy procedure. The Y-shaped implant aids vaginal cuff suspension to the sacrum and provides long-term support. The procedure can be minimally invasive (laparoscopic sacral colpopexy) or traditional (open sacral colpopexy). The existing Y-shaped implants may be made by joining two pieces of materials. This results in the formation of a junction or a seam between the two piece materials. Stress development along junctions can lead to failure, seam irritation or stiffness, and other similar problems in such implants. The process used for joining the two pieces also increases the manufacturing time and cost.

Thus, in light of the above, there is a need for an improved Y-shaped implant.

SUMMARY

In an embodiment, the invention discloses an implant that includes a first elongate member and a second elongate member formed monolithically with the first elongate member out of a single material and planar strip of material. The first elongate member includes a distal end portion and a proximal end portion. The second elongate member includes a first portion and a second portion. Further, each of the first portion of the second elongate member and the second portion of the second elongate member includes a proximal end portion and a distal end portion. The first portion and the second portion extend from the first elongate member. The distal end portion of the first elongate member is configured to be attached to or proximate a sacrum. The first portion and the second portion are configured to cover at least partially and be attached to a portion of the lateral walls of a vagina such that the first portion and the second portion extend longitudinally along the lateral walls of the vagina.

In an embodiment, the invention discloses a medical device. The medical device includes a Y-shaped implant, a sleeve covering at least a portion of the implant, and a dilator. The Y-shaped implant includes a first elongate member and a second elongate member. The first elongate member includes a distal end portion and a proximal end portion. The second elongate member is formed monolithically with the first elongate member out of a single and planar strip of material. The second elongate member includes a first portion and a second portion. Further, each of the first portion and the second portion includes a proximal end portion and a distal end portion, such that the first and second portions extend from the first elongate member. The dilator includes a proximal end portion and a distal end portion, such that the proximal end portion of the dilator is configured to be coupled to the implant.

In an embodiment, the invention discloses a method of implanting a medical device in a patient's body. The method comprises creating one of an anterior incision and a posterior incision at one of the anterior and posterior vaginal walls, respectively. The method includes inserting a Y-shaped implant inside the body trans-vaginally. The implant includes a first elongate member having a distal end portion and a proximal end portion and a second elongate member including a first portion and a second portion such that the second elongate member extend monolithically from the first elongate member. The method further includes attaching the first portion and the second portion to lateral portions of a vaginal wall such that the first portion and the second portion extend longitudinally down the lateral portions of the vaginal wall. The method further includes attaching a distal end portion of the first elongate member to or proximate to a sacrum.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

In general, the invention is directed to systems, methods, and devices for treating vaginal prolapse. However, the invention may be equally employed for other treatment purposes such as pelvic organ prolapse or other pelvic disorders. As described below in various illustrative embodiments, the invention provides systems, methods, and devices employing a medical device including an implant such that the implant is configured to be placed within a patient's body to support pelvic organs for the treatment of pelvic prolapse.

The term patient may be used hereafter for a person who benefits from the medical device or the methods disclosed in the present invention. For example, the patient may be a person whose body receives the medical device disclosed by the present invention in a surgical treatment. For example, in some embodiments, the patient may be a human female, human male or any other mammal.

The terms proximal and distal described in relation to various devices, apparatuses, and components as discussed in the subsequent text of the present invention are referred to with a point of reference. The point of reference, as used in this description, is a perspective of an operator. The operator may be a surgeon, a physician, a nurse, a doctor, a technician, and the like who may perform the procedure of delivery and placement of the bodily implants into the patient's body as described in the present invention. The term proximal refers to an area that is closest to the operator. The term distal refers to an area that is farthest from the operator.

Figure 1:
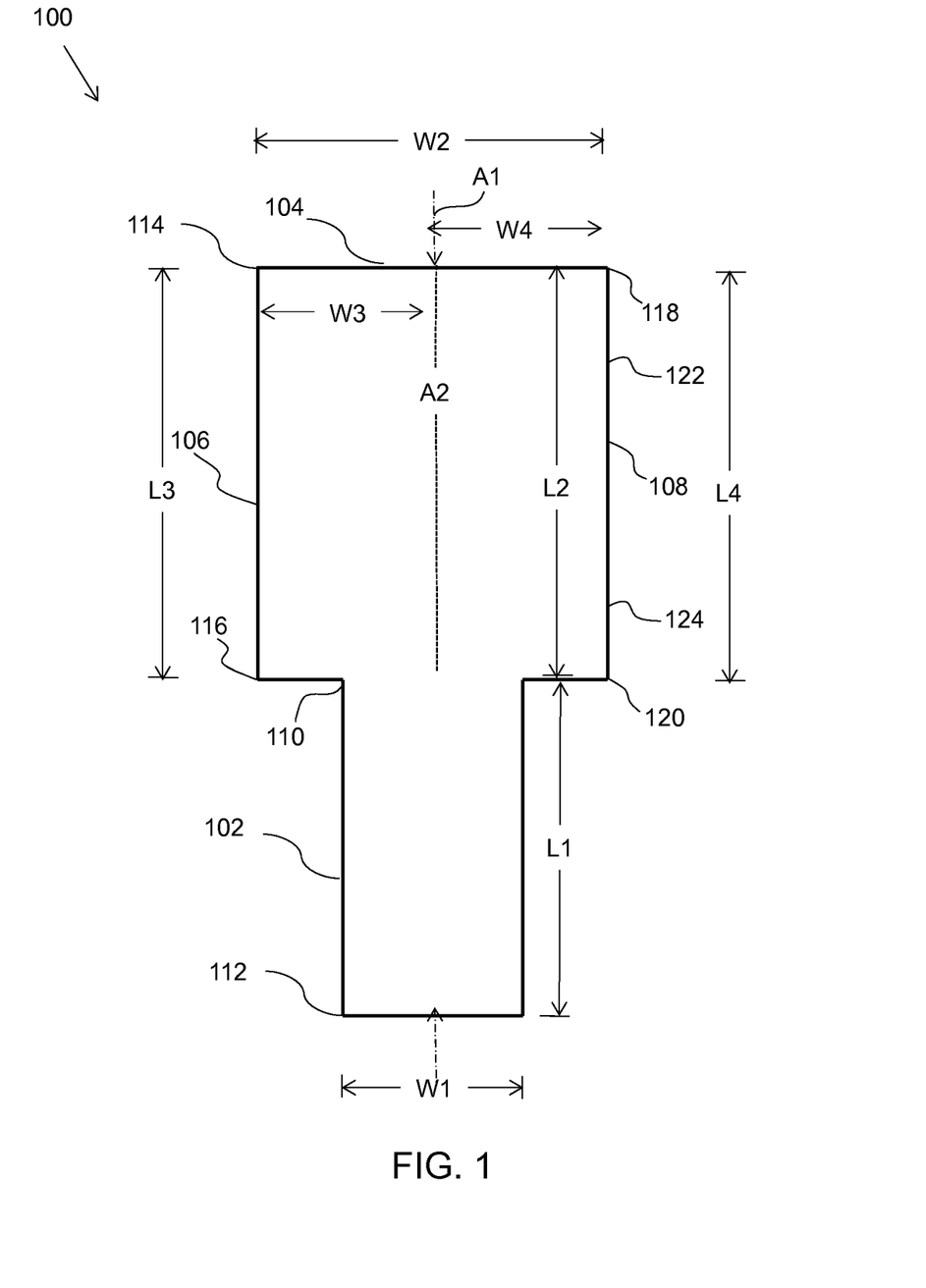
FIG. 1 illustrates a schematic diagram of an implant configured to be implanted within a patient's body, in accordance with an embodiment of the present invention.

FIG. 1 is a schematic diagram of an implant 100 configured to be placed within a patient's body. In some embodiments, the implant 100 is configured to support bodily tissues for the treatment of pelvic floor prolapse. The implant 100 includes a first elongate member 102 and a second elongate member 104 formed monolithically with the first elongate member 102 out of a single and planar strip or piece of material. The second elongate member 104 includes a first portion 106 and a second portion 108 such that both the first portion 106 and the second portion 108 extend from the first elongate member 102.

The first elongate member 102 includes a proximal end portion 110 and a distal end portion 112 with a length L1 extending between the proximal end portion 110 and the distal end portion 112. The first elongate member 102 includes a width W1. In accordance with some embodiments, the width W1 of the first elongate member 102 is uniform from the proximal end portion 110 to the distal end portion 112. In some other embodiments, the width W1 of the first elongate member 102 varies from the proximal end portion 110 to the distal end portion 112. In some embodiments, the first elongate member 102 is a strip with the length L1 substantially more than its width W1. In certain embodiments, the first elongate member 102 is rectangular in shape. In some other embodiments, the first elongate member 102 may have other shapes and sizes. For example, the first elongate member 102 may have a triangular shape, a bell shape, or any other shape.

The second elongate member 104 extends monolithically from the first elongate member 102. The second elongate member 104 includes a proximal end portion 122 and a distal end portion 124 with a length L2 extending between the proximal end portion 122 and the distal end portion 124. In some embodiments, the length L2 of the second elongate member 104 is lesser than the length L1 of the first elongate member 102. In some embodiments, the length L2 of the second elongate member 104 is half of the length L1 of the first elongate member 102. In some other embodiments, the length L1 of the first elongate member 102 and the length L2 of the second elongate member 104 can be the same. The second elongate member 104 includes a width W2. In accordance with some embodiments, the width W2 of the second elongate member 104 is uniform from the proximal end portion 122 to the distal end portion 124. In some other embodiments, the width W2 of the second elongate member 104 varies from the proximal end portion 122 to the distal end portion 124. In some embodiments, the second elongate member 104 has the width W2 equal to the width W1 of the first elongate member 102. In some embodiments, the second elongate member 104 has the width W2 lesser than the width W1 of the first elongate member 102. Further, in some other embodiments, the second elongate member 104 has the width W2 greater than the width W1 of the first elongate member 102. In some embodiments, the second elongate member 104 is a strip extended from the first elongate member 102 with its width W2 substantially less than its length L2. In certain embodiments, the second elongate member 104 is rectangular in shape. In some other embodiments, the second elongate member 104 may have other shapes. For example, the second elongate member 104 may have a triangular shape, a bell shape, or any other shape.

The second elongate member 104 includes the first portion 106 and the second portion 108 (as denoted by a dotted line A2 in FIG. 1) that extend from the first elongate member 102. In some embodiments, the first portion 106 and the second portion 108 can form an integral part of the second elongate member 104 that can extend monolithically from the first elongate member 102, thereby forming the implant 100 including the first and the second elongate members 102 and 104 made of a single material.

The first portion 106 includes a proximal end portion 114 and a distal end portion 116 with a length L3 extending between the proximal end portion 114 and the distal end portion 116. The second portion 108 includes a proximal end portion 118 and a distal end portion 120 with a length L4 extending between the proximal end portion 118 and the distal end portion 120. In some embodiments, the length L3 of the first portion 106 and length L4 of the second portion 108 can be the same. In some other embodiments, the lengths L3 and L4 can be different. The first portion 106 defines a width W3 and the second portion 108 defines a width W4. In some embodiments, the width W3 is equal to the width W4. In some embodiments, the width W3 is lesser than the width W4. Further, in some embodiments, the width W3 is greater to the width W4.

In some embodiments, the first portion 106 and the second portion 108 of the second elongate member 104 may be separated by a division or a partition or cut or slot provided longitudinally along a longitudinal axis A1. The division or cut can divide the implant 100 into three separately moveable arms defined by the first elongate member 102, the first portion 106, and the second portion 108. The three arms can be movable with respect to one another to conform to the shape of the target anatomical location of attachment inside the body. The three arms can take a shape such as linear/planar, curvilinear, curved, or any other shape and can conform to the target anatomical location of the patient where the first portion 106 and the second portion 108, and the first elongate member 102 are attached. Upon placement, the first portion 106 of the second elongate member 104, the second portion 108 of the second elongate member 104, and the distal end portion 112 of the first elongate member 102 act as three different arms that can be configured to support the pelvic organs by attaching the implant 100 at three distinct bodily locations.

Figure 4A:
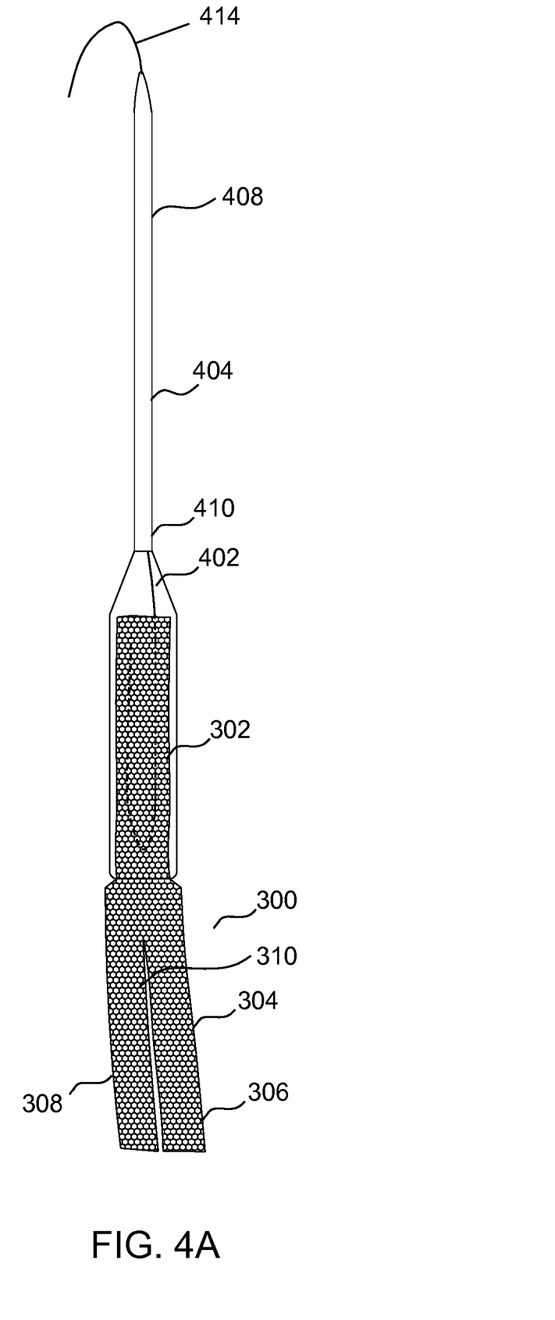
FIG. 4A illustrates a top view of an implant coupled to a dilator and a sleeve, in accordance with an embodiment of the present invention.

In some embodiments, the implant 100 can be prefabricated such that the cut separates the first portion 106 and the second portion 108 along one of their edges. In some embodiments, the implant 100 can be prefabricated such that the first portion 106 and the second portion 108 of the second elongate member 104 are not separated by the cut. In such cases, an operator may have the liberty to provide the cut before performing the operating procedure as per the requirements and thus, the width W3 and the width W4 can be varied by the operator prior to placement of the implant 100 based on the anatomical location of the patient where the first portion 106 and the second portion 108 are to be attached. Also, in such embodiments, the operator or surgeon may alter the length L1 of the first elongate member 102 at his discretion by varying the length of the cut along the second elongate member 104 longitudinally. Thus, in some embodiments, the operator may vary the length L1 and L2, and widths W3 and W4 at his discretion. In some embodiments, the lengths L1 and L2 can be 5 inches. In other embodiments, the lengths L1 and L2 can vary based on the requirement. In some embodiments, the widths W1, W2, and W3 can be 1.5 inches. In other embodiments, the widths W1, W2, and W3 can vary based on the requirement. Thus, in some embodiments, there are possibilities of defining the lengths and widths of various portions of the implant 100 as per the requirements by providing the cut. The implant 100 includes a thickness T (shown in FIG. 4). In some embodiments, the thickness T can be substantially smaller than the widths W1, W2 and W3. For example, in some embodiments, the thickness T can vary from 0.0078-0.0196 inches, whereas at least one of the widths W1, W2 and W3 can be 1.5 inches, though other values are also possible in some other embodiments. In such embodiments, as the thickness T is very small as compared to the widths W1, W2 and W3, therefore the implant 100 defines a planar-Y shape when viewed as a top view. In some embodiments, the thickness of the first portion 106, second portion 108, and the first elongate member 102 can be same or different.

In some embodiments, the cut can be defined or provided by removal of a piece of material between the first portion 106 and the second portion 108. In such cases, the cut can have a width (described later by FIG. 3 in a specific embodiment) such that there is a noticeable space between the first portion 106 and the second portion 108 due to removal of some portion of the material.

The first portion 106 and the second portion 108 of the second elongate member 104 are configured to cover at least partially and be attached to a portion of the lateral walls of a patient's vagina such that the first portion 106 and the second portion 108 extend longitudinally down the lateral walls of the vagina. In accordance with these embodiments, the first portion 106 of the second elongate member 104 is, for example, attached to a first lateral wall of the vagina and the second portion 108 of the second elongate member 104 is attached to a second lateral wall of the vagina.

In some embodiments, the procedure of the implant 100 within the body can be performed after performing hysterectomy and removal of uterus from the body. In such cases, where a uterus of the patient is removed, the first portion 106 and the second portion 108 are attached to the vaginal cuff of the patient or a location proximate the vaginal cuff of the patient. In some embodiments, the first portion 106 and the second portion 108 are attached to the vaginal cuff at 3 o'clock and 9 o'clock positions when viewed in a front view along the vaginal opening. In some other embodiments where the uterus is intact, the first portion 106 and the second portion 108 are attached to the vaginal apex of the patient or a location proximate the vaginal apex of the patient. The distal end portion 112 of the first elongate member 102 is configured to be attached to or proximate to a sacrum of the patient.

The first elongate member 102, the first portion 106, and the second portion 108 of the second elongate member 104 can be attached inside the patient's body through various attachment elements or means. In some embodiments, the attachment elements include, without limitations, sutures, adhesives, bonding agents, mechanical fasteners (e.g. a medical grade plastic clip), staples, and the like. In some embodiments, the implant can be sutured to bodily tissues with the use of a suturing device such as a Capio™ (as sold and distributed by Boston Scientific Corporation) and the like.

In some embodiments, the implant 100 can be delivered inside a patient's body using any suitable insertion tool such as a needle or any other device. In some embodiments, a dilator may be attached to the implant 100 and used to deliver the implant 100 inside the patient's body.

In various embodiments, as discussed above, the implant 100 is made of a single piece of material. In some embodiments, the material is synthetic. In some embodiments, the implant includes a polymeric mesh body. Exemplary polymeric materials are polypropylene, polyester, polyethylene, nylon, PVC, polystyrene, and the like. In some other embodiments, the implant includes a polymeric planar body without mesh cells. In some embodiments, the implant is made of a mesh body made of a non-woven polymeric material. An example of the mesh, out of which the single piece implant is formed, can be Polyform® Synthetic Mesh developed by the Boston Scientific Corporation. The Polyform® Synthetic Mesh is made from uncoated monofilament macro-porous polypropylene. In some embodiments, the mesh weight of the implant can be approximately between 15 $g/cm^2$ to 35 $g/cm^2$ (e.g., 20 $g/cm^2$, 25 $g/cm^2$, 30 $g/cm^2$). In other embodiments, the mesh weight of the implant is greater than 35 $g/cm^2$. Typically, the surface of the implant 100 is made smooth to avoid/reduce irritation on adjacent body tissues during medical interactions. Additionally, the implant is stretchable and flexible to adapt movements along the anatomy of the human body and reduce suture pullout. Furthermore, softness, lightness, conformity, and strength are certain other attributes that can be provided in the implant for efficient tissue repair and implantation. In some embodiments, as discussed additionally below, the implant 100 can be made of natural materials such as biologic material or a cadaveric tissue and the like. Exemplary biologic materials are bovine dermis, porcine dermis, porcine intestinal sub mucosa, bovine pericardium, a cellulose based product, cadaveric dermis, and the like.

In some embodiments, the implant 100 may be formed of a sheet type material. The sheet may include pore or may be substantially solid. In some embodiments, the sheet type material may be porous or non-porous. In some embodiments, at least a portion of the implant 100 can be made of a biologic material such as an Allograft and/or a Xenograft. In some implementations, the biologic material can include cadaveric tissue, bovine dermis, porcine dermis, porcine intestinal sub mucosa, bovine pericardium, a cellulose based product, cadaveric dermis, and/or so forth. In some implementations, the Allograft materials can include Tutoplast®, Repliform®, DuraDerm®, Urogen®, and/or so forth. In some implementations, the Xenograft materials can include Xenoform® (e.g., Xenoform Matrix), Stratisis®, Dermatrix® and/or so forth. In some implementations, the implant 100 can be made of a biologic material because the biologic material can be relatively robust against tissue erosion.

Figure 2:
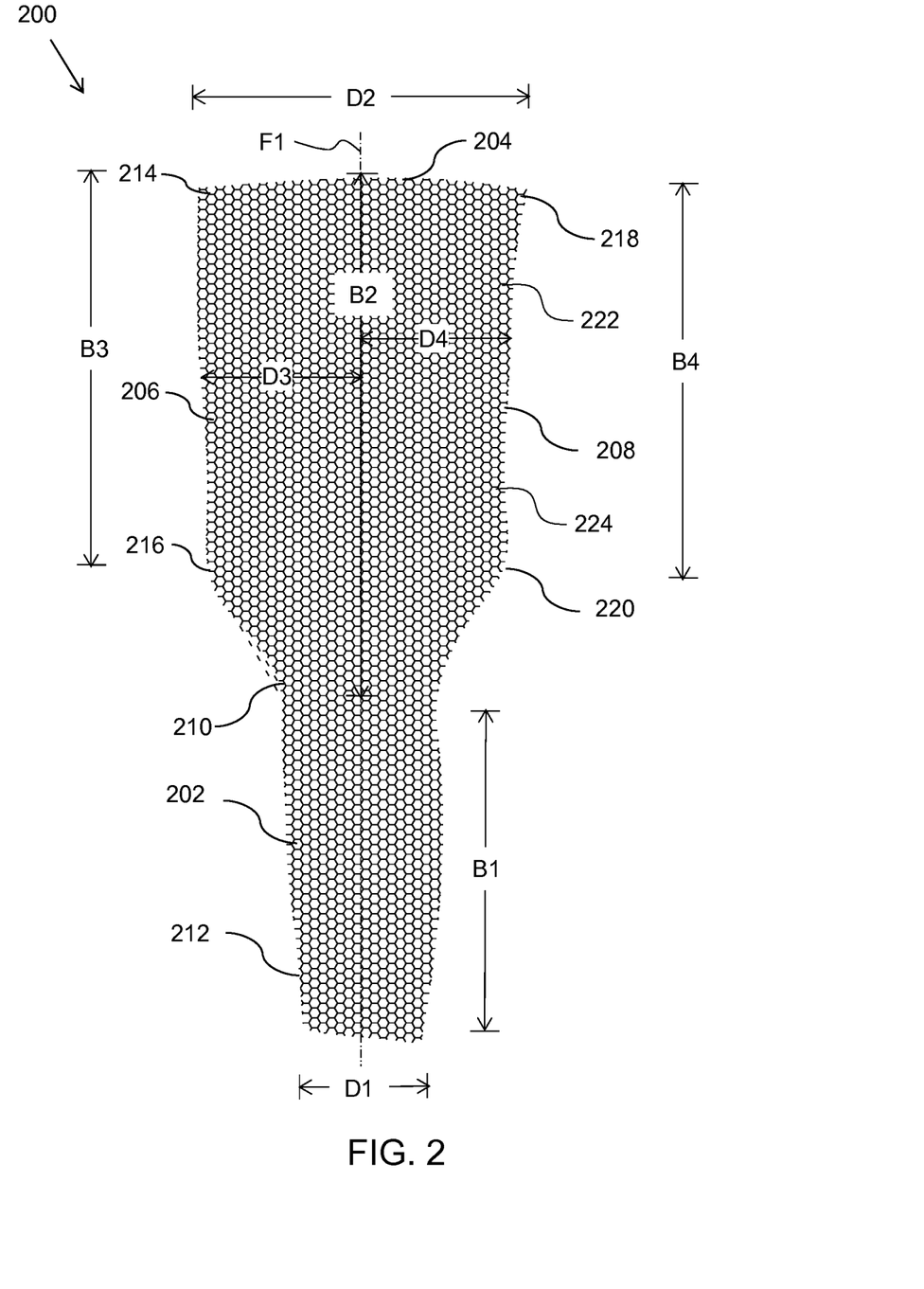
FIG. 2 illustrates a top view of an implant configured to be placed within a patient's body, in accordance with an embodiment of the present invention.

FIG. 2 is a perspective view of an implant 200 configured to be placed into a patient's body, in accordance with an embodiment of the present invention. The implant 200 includes a first elongate member 202 and a second elongate member 204 formed monolithically with the first elongate member 202 out of a single and planar strip or piece of material. The second elongate member 204 includes a first portion 206 and a second portion 208 such that both the first portion 206 and the second portion 208 extend monolithically from the first elongate member 202, thereby forming the implant 200 including the first and the second elongate members 202 and 204 made of a single material.

The first elongate member 202 includes a proximal end portion 210 and a distal end portion 212 with a length B1 extending between the proximal end portion 210 and the distal end portion 212. The first elongate member 202 includes a width D1. In accordance with the illustrated embodiments, the width D1 of the first elongate member 202 is uniform from the proximal end portion 210 to the distal end portion 212. In some other embodiments, the width D1 of the first elongate member 202 can vary as discussed in FIG. 1. In some embodiments, as illustrated, the first elongate member 202 is a strip with the length B1 substantially more than its width D1. As illustrated, the first elongate member 202 is rectangular in shape. In other embodiments, the first elongate member 202 may have other shapes.

The second elongate member 204 extends monolithically from the first elongate member 202 as the first elongate member 202 and the second elongate member 204 are formed of a single piece of material. The second elongate member 204 includes a proximal end portion 222 and a distal end portion 224 with a length B2 extending between the proximal end portion 222 and the distal end portion 224. In the illustrated embodiment, the length B2 of the second elongate member 204 is more than the length B1 of the first elongate member 202. In some embodiments, however, the length B2 can vary as discussed in some other embodiments in FIG. 1. The second elongate member 204 includes a width D2. In accordance with some embodiments as illustrated, the width D2 of the second elongate member 204 is uniform from the proximal end portion 222 to almost the distal end portion 224 with a taper at the distal end portion 224 that extends to the first elongate member 202. The taper can be defined by a smooth curved profile in some embodiments. In some embodiments, the second elongate member 204 has the width D2 greater than the width D1 of the first elongate member 202.

The second elongate member 204 includes the first portion 206 and the second portion 208 that extend from the first elongate member 202 such that the distal end portion 224 of the second elongate member 204 is proximate to the proximal end portion 210 of the first elongate member 202.

The first portion 206 includes a proximal end portion 214 and a distal end portion 216 with a length B3 extending between the proximal end portion 214 and the distal end portion 216. The second portion 208 includes a proximal end portion 218 and a distal end portion 220 with a length B4 extending between the proximal end portion 218 and the distal end portion 220. In some embodiments, the length B3 of the first portion 206 and the length B4 of the second portion 208 can be almost the same (as shown), but other embodiments are also possible as discussed in FIG. 1. The first portion 206 defines a width D3 and the second portion 208 defines a width D4 at their distal portions.

A portion of the implant 200 shown in FIG. 2 can be linearly or in any other shape cut by making a division or cut such as longitudinally or in any other pattern along the length B2 of the second elongate member 204 to separate the first portion 206 from the second portion 208 before performing the procedure. This can then convert the implant 200 into a three arm-based implant such that each arm can be positioned at one distinct location inside the body. In some embodiments, the operator or surgeon may define lengths and widths of the first and second portions 206 and 208 by providing a cut in the implant 200 before the procedure. In these embodiments, the first portion 206 can be folded over to the second portion 208 along a longitudinal axis F1 such that the first portion 206 has the freedom or reach to be attached to a vaginal cuff on a posterior side and the second portion 208 can be attached to an anterior side of the vaginal cuff or a location proximate the vaginal cuff of the patient. Thus the first portion 206 and the second portion 208 can be attached to the vaginal cuff or a location proximate the vaginal cuff of the patient distributed at several locations so as to reduce implant load in the vagina. The first elongate member 202 and the second elongate member 204 collectively define a planar Y-shape as illustrated in FIG. 2. Upon placement, the first portion 206 of the second elongate member 204, the second portion 208 of the second elongate member 204 (that may be separated right before the implantation), and the distal end portion 212 of the first elongate member 202 act as three different arms of the implant and are configured to support the pelvic organs at three distinct bodily locations. In accordance with these embodiments, the first portion 206 forms a first arm, the second portion 208 forms a second arm, and the distal end portion 212 of the first elongate member 202 forms a third arm of the implant.

The first portion 206 and the second portion 208 of the second elongate member 204 are configured to cover at least partially and be attached to a portion of lateral walls of a vagina such that the first portion 206 and the second portion 208 extend longitudinally down the portion of lateral walls of the vagina. For example, in accordance with these embodiments, the first portion 206 of the second elongate member 204 is attached to a first lateral wall of the vagina and the second portion 208 of the second elongate member 204 is attached to a second lateral wall of the vagina.

In some embodiments, the procedure of attachment of the implant 200 within the body can be performed after performing hysterectomy and removal of uterus from the body. In such cases, where the patient's uterus is removed, the first portion 206 and the second portion 208 are attached to the vaginal cuff of the patient or a location proximate the vaginal cuff of the patient. In some other embodiments, where the uterus is intact, the first portion 206 and the second portion 208 are attached to the vaginal apex of the patient or a location proximate the vaginal apex of the patient. The distal end portion 212 of the first elongate member 202 is configured to be attached to or proximate to the patient's sacrum.

In some embodiments, the implant 200 can be made of materials such as discussed in conjunction with FIG. 1, without limitations.

The shape of the first elongated member 202 and the second elongate member 204 described in conjunction with FIG. 2 is merely exemplary and various other shapes and designs are also possible, in accordance with various embodiments of the present invention.

Figure 3:
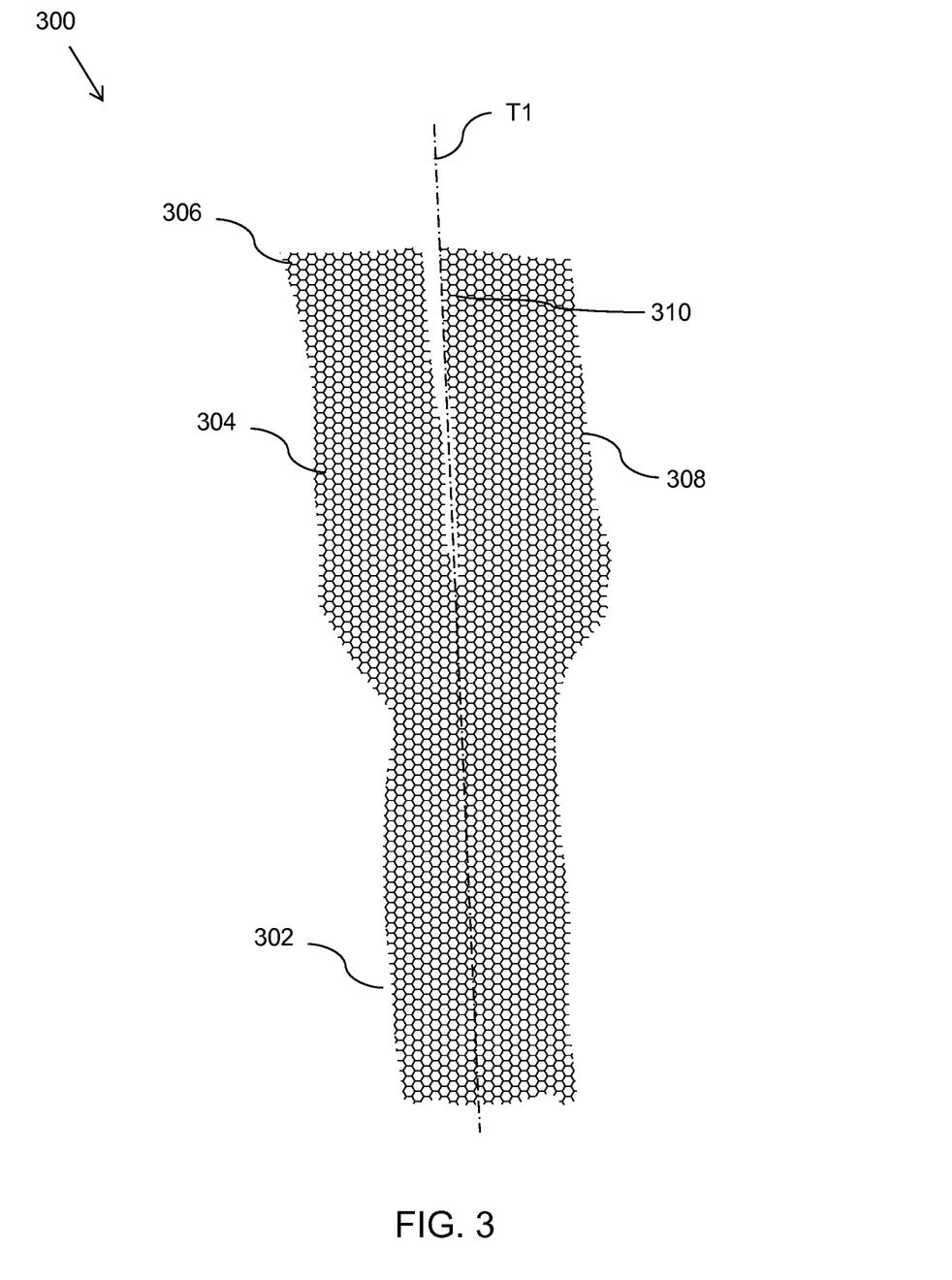
FIG. 3 illustrates a top view of an implant configured to be placed within a patient's body, in accordance with an embodiment of the present invention.

FIG. 3 is a perspective view of an implant 300, in accordance with an embodiment of the present invention. The implant 300 includes a first elongate member 302 and a second elongate member 304 formed monolithically with the first elongate member 302 and made of a single piece of material. The second elongate member 304 includes a first portion 306 and a second portion 308. The first portion 306 and the second portion 308 extend from the first elongate member 302. The first elongate member 302 is similar to those described in conjunction with FIG. 2 above.

As is evident, the implant 300 is similar to the implant 200 of FIG. 2 except that the implant 300 is prefabricated with a cut or division 310 separating the first portion 306 from the second portion 308 along one of their edges. In some embodiments. The cut 310 is provided longitudinally along a longitudinal axis T1 and extending along the edges of the first portion 306 and the second portion 308. The cut divides the second elongate member 304 into two arms that can take a define shape. In some embodiments, the cut 310 can be made in a direction other than along the longitudinal axis such as in a zigzag pattern or oriented away from the longitudinal axis.

The cut 310 divides the entire implant 300 into three arms so that the three arms can be attached to three distinct locations. In the illustrated embodiment, the implant 300 is fabricated as an integral Y-shaped mesh out of a single and planar strip of material without any junction or coupling of multiple pieces of material. As is evident from the top view of the implant 300, depicted in FIG. 3, the three arms of the Y-shaped implant defines planar surfaces so as to form a planar Y-shaped implant 300 as viewed in the top view. In accordance with some other embodiments, the implant 300 can be fabricated even with the use of multiple pieces of material and coupled together at a junction. However, in such cases, the three arms of the implant 300 defines planar surfaces forming a planar Y-shape as opposed to a non-planar shape (with three arms merely defining almost three lines) when the implant is viewed in the top view similar to the view of the implant 300 of FIG. 3. In an embodiment, the width of the implant 300 can be substantially more than the thickness. In such embodiments, the implant 300 defines a planar-Y shape when viewed as a top view.

In the illustrated embodiment, the cut 310 is defined by removal of a piece of material between a first portion 306 and a second portion 308 in a defined shape. In some embodiments, the defined shape can be a U shape or V shape. However, other possible shapes such as rectangular, triangular or any other shape may also be possible in some other embodiments.

Figure 4B:
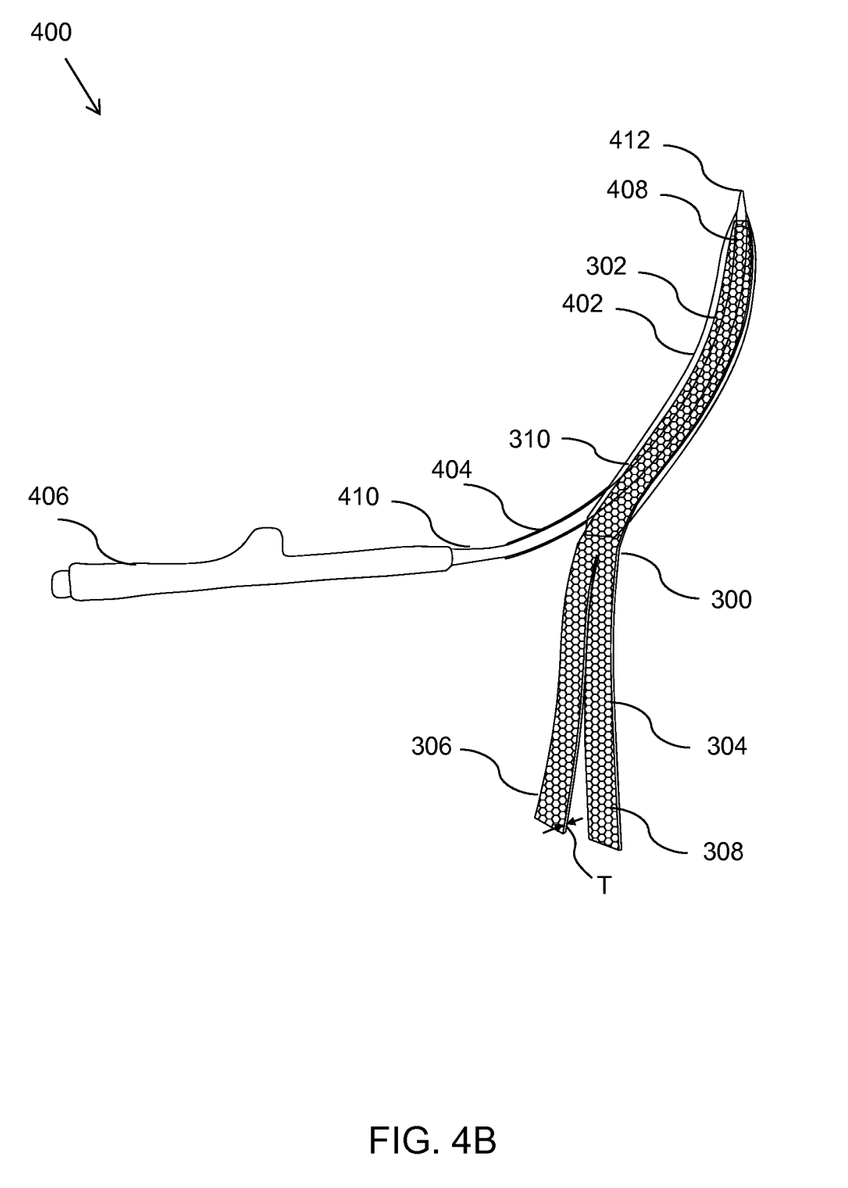
FIG. 4B illustrates a perspective view of an implant coupled to a dilator and an insertion tool for delivery and placement of the implant within a patient's body, in accordance with an embodiment of the present invention.

FIG. 4A illustrates a top view of the Y-shaped planar implant 300 coupled to a dilator 404, and a sleeve 402. FIG. 4B illustrates a perspective view of a medical device 400, in accordance with an embodiment of the present invention. The medical device 400 includes the Y-shaped implant 300, the sleeve 402, the dilator 404, and an insertion tool 406. The implant 300 is referred to for the purpose of description hereafter; however, any other implant (as discussed above) can be used in some embodiments. Referring now to FIGS. 4A and 4B, the implant 300 and the medical device 400 are described.

The sleeve 402 may be a protective sheath or covering that is placed over the implant 300 and coupled to the implant 300 with the use of such as a suture 414 extending along a portion of the sleeve 402 and through the dilator 404. In the illustrated embodiments, the sleeve 402 is placed over the first elongate member 302 as illustrated in FIG. 4A. The sleeve 402 may be designed to minimize risk of contamination and reduce abrasive sliding of the implant 300 through a tissue. The sleeve 402 may be particularly desirable when the implant 300 is elastic as the sleeve 402 assists in introducing the implant 300 within the tissue and avoids damage to the material of the implant 300. After the implant 300 is delivered and placed, the sleeve 402 is removed and discarded, in some embodiments.

The dilator 404 can be used to facilitate delivery of the implant 300 into the patient's body. The dilator 404 includes a proximal end portion 408 and a distal end portion 410 such that the distal end portion 408 of the dilator 404 is configured to be coupled to the implant 300 and the proximal end portion 410 of the dilator can be manipulated by the operator. In some embodiments, the dilator 404 is removably coupled to the implant 300. In other embodiments, the dilator 404 is fixedly coupled to the implant 300. In some embodiments, the dilator 404 has a tapered shape at its tip such that it is configured to dilate or expand an opening or a passage within a bodily tissue. In some other embodiments, the dilator 404 can be a thin shaped tubular member without a taper but configured to dilate the tissue because of its thin and sharp nature. The dilator 404 is configured to be attached to a delivery device such as the insertion tool 406. The insertion tool 406 includes a needle 412 that is configured to be coupled to the dilator 404 and deliver the implant 300 within the patient's body through such as a trans-vaginal procedure. In an embodiment, the dilator 404 and the sleeve 402 are coupled to the same arm of the implant such as the first elongate member 302 defining the first arm.

In some embodiments, the delivery device can be any conventionally used delivery device such as a surgical needle or a suturing type device discussed below. In some embodiments, the dilator 404 can be sized to accept a step needle delivery device such as the Solyx™ delivery device as sold by Boston Scientific Corporation, or the dilator 404 can be sized and lengthened to be fitted to an Advantage™ delivery device as sold by Boston Scientific Corporation. In certain embodiments, the dilator 404 can be sized or lengthened to be fitted to an Advantage™ delivery device.

Figure 5A:
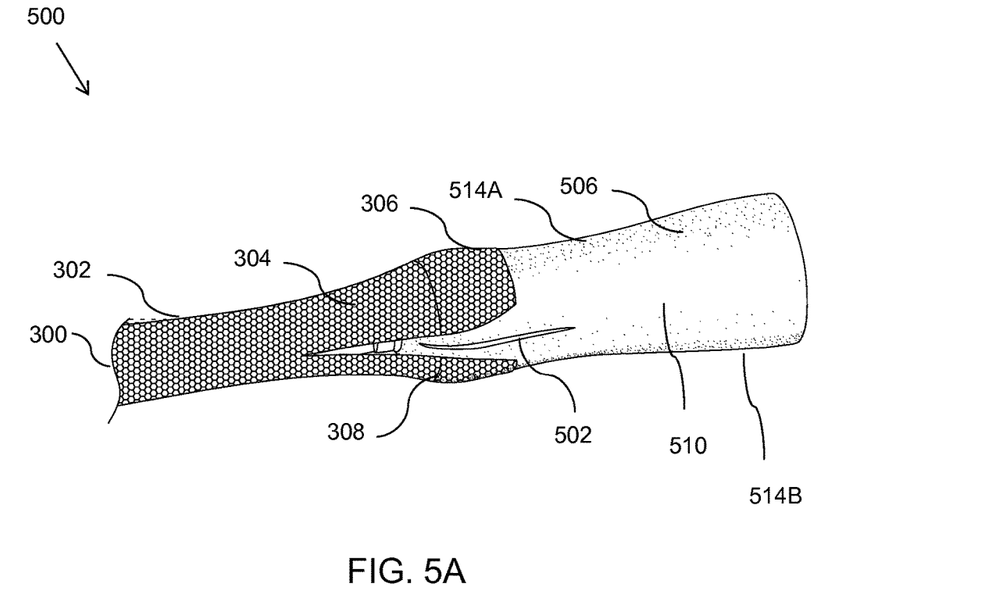
FIG. 5A illustrates a schematic view of placement of an implant within a patient's body through an anterior incision, in accordance with an embodiment of the present invention.
Figure 5B:
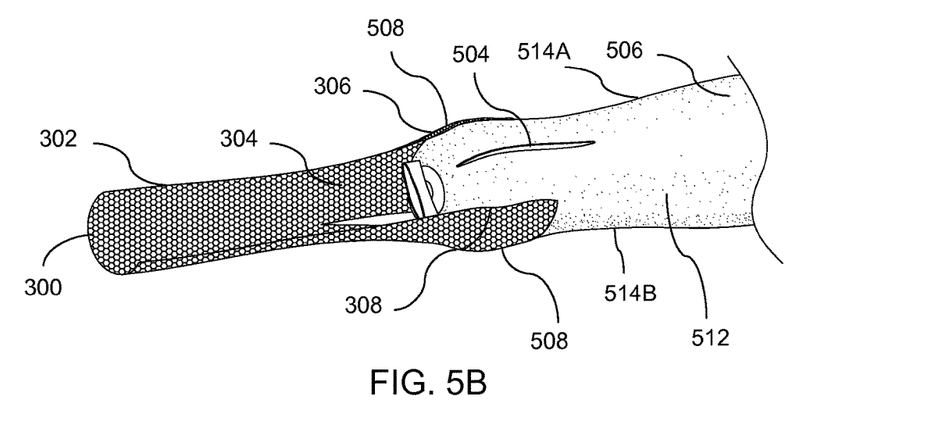
FIG. 5B illustrates a schematic view of the placement of the implant of FIG. 5A within a patient's body through a posterior incision, in accordance with an embodiment of the present invention.

FIGS. 5A-5B illustrate schematic views of a portion of the implant 300 as placed within a patient's body over a first lateral wall 514 A of a vagina 508 and a second lateral wall 514B of a vagina 508, in accordance with an embodiment of the present invention. FIG. 5A illustrates a schematic view of the implant 300 placed within a patient's body through an anterior incision 502, in accordance with an embodiment of the present invention. FIG. 5B illustrates placement of the implant 300 within a patient's body through a posterior incision 504, in accordance with an embodiment of the present invention. FIGS. 5A and 5B illustrate a view in which the patient's uterus is removed. However, in some other embodiments, the procedure can be performed with the uterus in place within the body. The body portions of the patient such as the vagina 508, a vaginal cuff 506, an anterior portion of vagina 510, and a posterior portion of vagina 512 are illustrated in FIGS. 5A and 5B.

As shown, the first portion 306 and the second portion 308 of the second elongate member 304 are secured to the vaginal cuff 506 or a location proximate the vaginal cuff of the patient. The distal end portion of the first elongate member 302 is attached to or proximate to the sacrum (not shown in FIGS. 5A and 5B).

In some embodiments, the anterior incision 502 may be a single long incision as illustrated in FIG. 5A. In some embodiments, the posterior incision 504 may be a single long incision as illustrated in FIG. 5B. In such cases, the anterior incision 502 and/or the posterior incision 504 may allow access for lights or suction or scopes or other types of instruments such as the delivery device mentioned above and the like. In some embodiments, only one of the anterior and posterior incisions may be provided. In some other embodiments, both anterior and posterior incisions 502 and 504 may be provided. In still some other embodiments, only one long incision extending from the anterior to the posterior portions 510 and 512 may be provided.

Figure 6A:
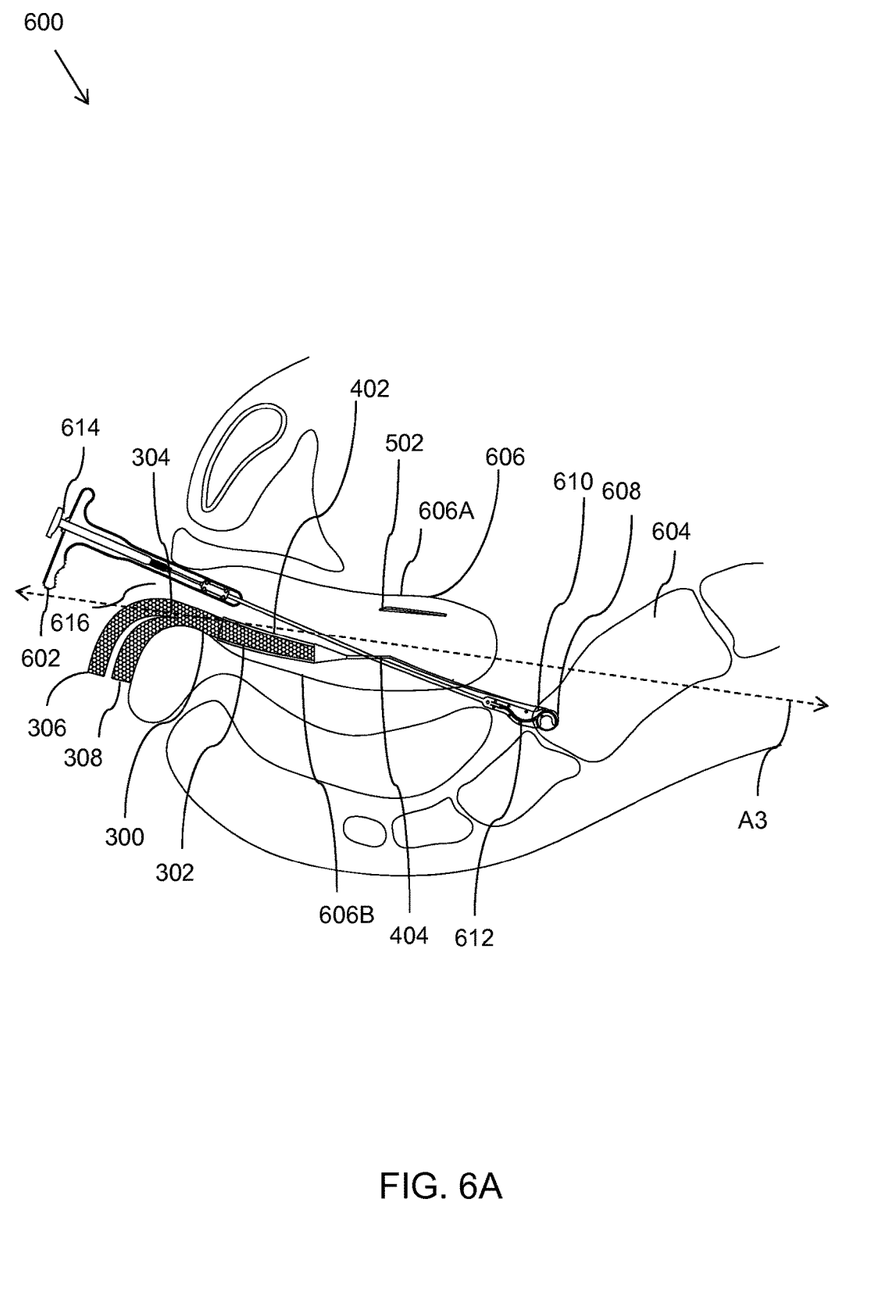
FIG. 6A illustrates placement of an implant within a patient's body with a suturing device, in accordance with an embodiment of the present invention.

FIG. 6A illustrates placement of the implant 300 within a patient's body using a suturing device 602. As illustrated, the suturing device 602 may be a delivery device for such as a blind suture engagement. The suturing device 602 may further include a suture 612 coupled to the implant 300, and the suturing device 602 may be configured to fix the implant 300 at a bodily location such as a sacrum 604 or locations proximate the sacrum 604.

In some embodiments, the suturing device can be a Capio™ delivery device (also referred to as Capio™ or Capio™ device) sold by Boston Scientific Corporation.

The different parts of the suturing device 602 such as a rotating head 608, a needle driver 610, and a needle driver button 614 are illustrated in FIG. 6A. In some embodiments, the first portion 306 and the second portion 308 of the second elongate member 304 may be attached to the lateral vaginal walls 606 with the use of such as a hand held needle or an insertion tool similar to the tool 400 (not illustrated in FIG. 6A) that can suture the implant 300 to the lateral vaginal walls 606. The first elongate member 302 may be configured to be attached to or proximate to the sacrum 604 with the use of the suturing device 602 such as through a blind suture engagement technique that the Capio™ is capable of. In embodiments, the suturing device 602 extends through the vaginal incision such as the posterior incision and up to the sacrum 604 or proximate the sacrum 604. The posterior incision lies at a location posteriorly to the vaginal opening 616 and is not visible in FIG. 6A.

Figure 6B:
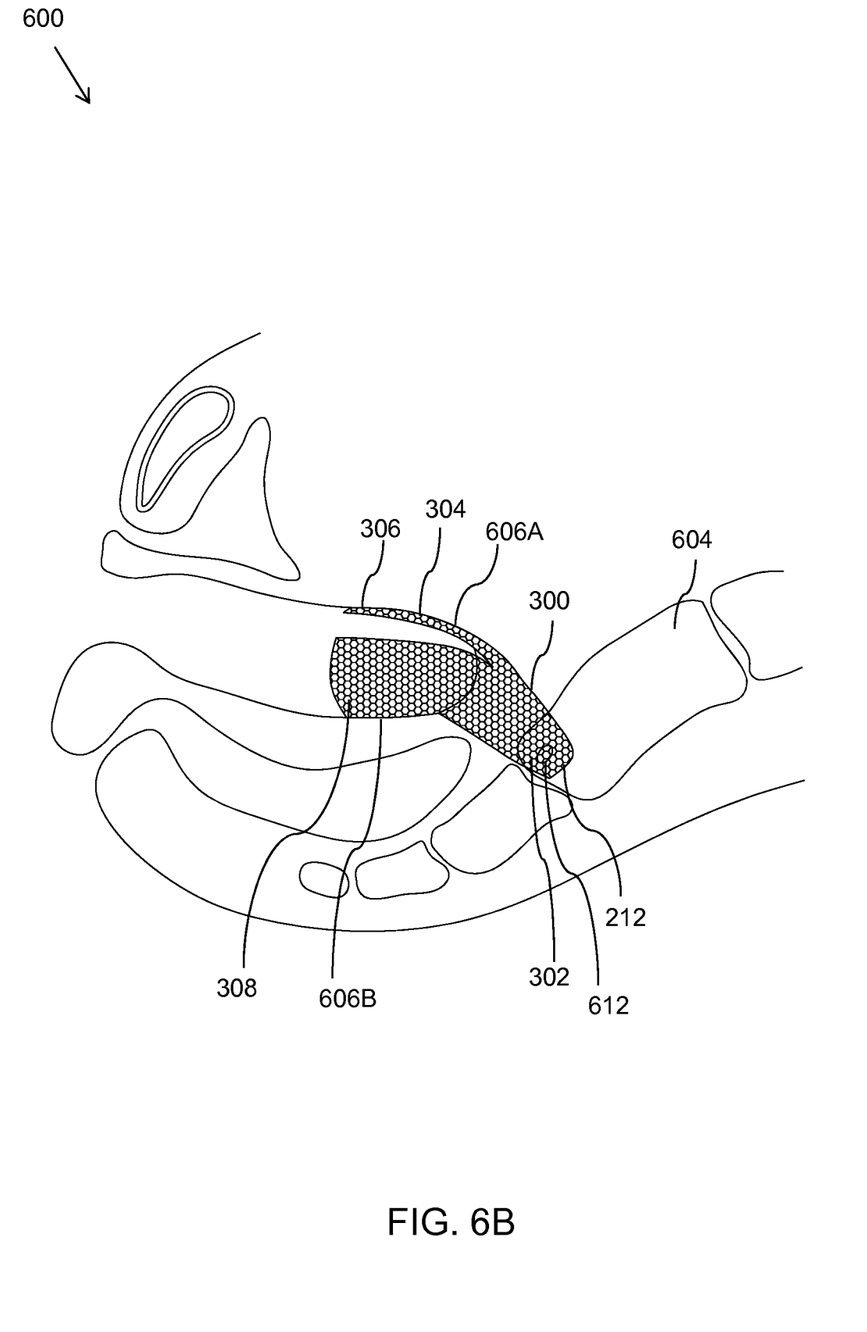
FIG. 6B illustrates the implant from FIG. 6A placed and sutured within a patient's body, in accordance with an embodiment of the present invention.

FIG. 6B illustrates the implant 300 positioned and placed in the body after the completion of the procedure. As shown, the first portion 306 and the second portion 308 are secured to the vaginal walls 606A and 606B laterally and the first elongate member 302 is sutured to the sacrum 604 or locations proximate the sacrum 604 of the patient. The suture 612 may fix the implant 300 at the sacrum 604 or proximate to the sacrum 604.

As shown, the first portion 306 of the second elongate member 304 covers at least partially and is attached to the first lateral wall 606A of the vagina and the second portion 308 of the second elongate member 304 is configured to cover at least partially and be attached to the second lateral wall 606B of the vagina, such that the first portion 306 and second portion 308 extend longitudinally down the first and second lateral walls 606A and 606B, respectively, in a direction parallel to a longitudinal axis A3 of vagina. The distal end portion 212 of the first elongate member 302 is configured to be attached to or proximate to the sacrum 604.

Figure 7:
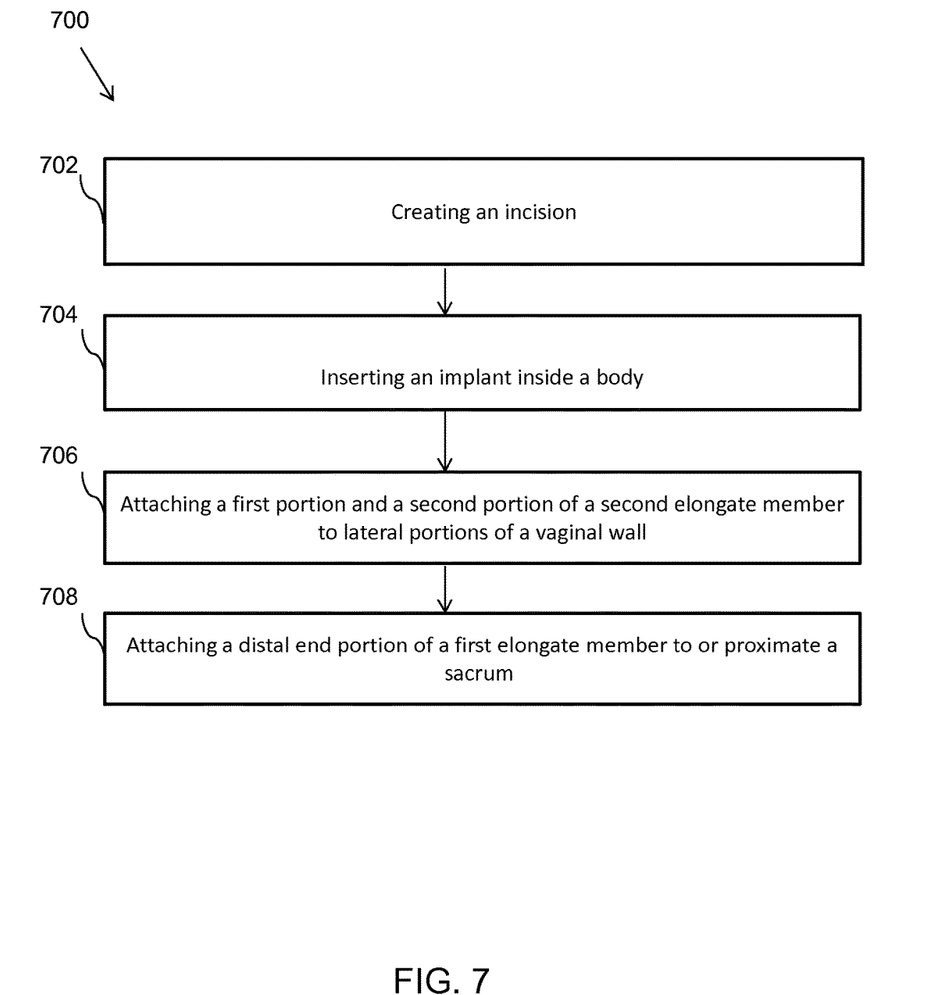
FIG. 7 is a flowchart illustrating a method of placing an implant in a patient's body, in accordance with an embodiment of the present invention.

FIG. 7 is a flowchart illustrating a method 700 of implantation of an implant such as the implant 300, in accordance with an embodiment of the present invention.

Referring to FIG. 7 in conjunction with FIGS. 3, 4A, 4B, 6A, and 6B, the method of placement of the implant 300 is described in accordance with an embodiment of the present invention. The implant 300 is hereafter used to describe the placement in an exemplary embodiment. However, it must be appreciated that other implants discussed above may also be placed in a similar manner.

The method 700 includes creating an incision, such as a vaginal incision or other bodily incision, at step 702. A vaginal incision can be one of the anterior incision 502 and the posterior incision 504 at one of the anterior vaginal wall 510 and the posterior vaginal wall 512 of a patient for delivery of the implant 300. In accordance with various embodiments, an operator/a surgeon may make incisions laproscopically, laprotomically, or in any other manner to create access to the vagina. Further, in some embodiments, the implant 300 is coupled to the dilator 404 and the insertion tool 406 for delivery and placement of the implant as discussed above in FIG. 4.

Once the access to the vagina is created, the Y-shaped implant 300 is inserted into a body of a patient at step 704. In some embodiments, the implant 30 is inserted trans-vaginally into the patient's body. The second elongate member 304 is either already separated into two portions during the fabrication stage or can be separated by the operator before procedure by making a cut to configure the implant 300 as a Y-shape implant with three arms for attachment at three locations. Therefore, in some embodiments, the method may include cutting the second elongate member 304 such as to define two arms from the second elongate member 304 that are separated at their proximal end portions 220 and 214, and coupled together at their distal end portions 220 and 216.

Subsequently, the method includes attaching the first portion 306 and the second portion 308 of the second elongate member 304 to a portion of lateral walls 606A and 606B of the vagina trans-vaginally through one of the anterior incision 502 and the posterior incision 504 at step 706. In some embodiments, the first portion 306 covers at least partially and is attached to the first lateral wall 606A of the vagina, and the second portion 308 covers at least partially and is attached to the second lateral wall 606B of the vagina such that the first and second portions 306 and 308 extend longitudinally down the first and second lateral walls 606A and 606B.

The method then includes attaching the distal end portion 212 of the first elongate member 302 to or proximate to the sacrum 604 at step 708. In some embodiments, the distal end portion 212 of the first elongate member 302 may be attached to the sacrum 604 trans-vaginally through one of the anterior incision 502 and the posterior incision 504. In some embodiments, the distal end portion 212 of the first elongate member 302 may be attached to the sacrum 604 laprosopically through an abdominal incision. In some embodiments, the implant 300 may be associated to the delivery device or suturing device 602 and can be re-inserted through the anterior incision 502 to secure and tension the first elongate member 302 to the sacrum 604 or proximate to the sacrum 604. After tensioning, the implant 300 can be trimmed and the delivery device 602 can be removed. The anterior and/or posterior incisions 502 and 504 are closed.

As discussed above, in some embodiments, the implant 300 can be delivered with the use of the insertion tool 406 coupled to the dilator 404. In such cases, the method may further include removing the dilator 404 from the body after the delivery of the implant 300 within the body. Further, in some cases, the implant 300 or at least one of the arms of the implant 300 that is configured to be attached to the sacrum or proximate the sacrum 604 may be covered with the sleeve 402. In such embodiments, the method may include removing the sleeve 402 from the body after placement of the implant 300. Also, in some cases, the sleeve 402 may be made of biologic material capable of being dissolved in the body such that there may not be any need to remove the sleeve 402 from the body. Also, in some cases, the suturing device 602 may be used to such as to suture the first elongate member 302 of the implant 300 to the sacrum 604 or close to the sacrum 604 with the use of blind suture engagement technique. Though the suturing device 602 can be used to couple the first portion 306 and the second portion 308 to the vaginal walls 606, the attachment of these portions on the vaginal walls 606 may not require a blind suturing technique and can simply be performed with the use of such as a simple handheld needle or any other tool.

In accordance with some embodiments, upon attachment of the implant 300 to target bodily locations, the method may further include trimming an unwanted portion of the implant 300.

The attachment of the implant 300 to the target body locations with sutures 612 may provide a desired tension to the implant 300. The tensioning of the implant 300 may appropriately be provided for the repair of pelvic floor disorder. Finally, the method includes removal of the insertion tool 406 and the suturing device 602 after delivery and placement of the implant 300 inside the body, and closing the anterior, posterior and laparoscopic incisions.

In some embodiments, the vagina 508 can be inverted to allow the first portion 306 and the second portion 308 of the implant 300 to be sutured or attached to the lateral areas of the vaginal cuff 506 or a location proximate the vaginal cuff of the patient. The first elongated member 302 of the implant 300 is then tucked or sutured into the anterior incision 502 before the incision is closed for later external access through the vagina 508. The anterior incision 502 can be closed with the suture or other means and the vagina 508 can be re-inverted back into its initial anatomical position. The first elongate member 302 can be accessed from the vagina 508 and associated to the delivery device 400 or 602 for securing to or proximate the sacrum 604. In some embodiments as illustrated in FIGS. 6A and 6B, the anterior incision 502 and posterior incision 504, respectively, are illustrated as unobstructed by the implant 300 with the first elongate member 302 oriented in a substantially flat configuration.

In some embodiments, an implant includes a first elongate member including a distal end portion and a proximal end portion; and a second elongate member formed monolithically with the first elongate member out of a single planar strip of material. The second elongate member includes a first portion and a second portion. Each of the first portion of the second elongate member and the second portion of the second elongate member includes a proximal end portion and a distal end portion. The first portion and the second portion extend from the first elongate member. The distal end portion of the first elongate member is configured to be attached to or proximate a sacrum. The first portion and the second portion are configured to cover at least partially and be attached to a portion of lateral walls of a vagina such that the first portion and the second portion extend longitudinally along the lateral walls of the vagina.

In some embodiments, the first elongate member and the second elongate member collectively define a planar Y-shape. In some embodiments, the implant is configured to be delivered inside a body of a patient through a vaginal incision. In some embodiments, the implant is configured to be delivered inside a body of a patient through a laparoscopic procedure. In some embodiments, the first portion is configured to cover at least partially and be attached to a first lateral wall of the vagina, and the second portion is configured to cover at least partially and be attached to a second lateral wall of the vagina such that the first and second portions extend longitudinally down the first and second lateral walls respectively.

In some embodiments, a medical device includes a Y-shaped implant having a first elongate member having a distal end portion and a proximal end portion; and a second elongate member formed monolithically with the first elongate member out of a single and planar strip of material. The second elongate member having a first portion and a second portion. Each of the first portion and the second portion of the second elongate member includes a proximal end portion and a distal end portion. The first portion and the second portion extend from the first elongate member. The device includes a sleeve covering at least a portion of the implant; and a dilator including a proximal end portion and a distal end portion. The proximal end portion of the dilator is configured to be coupled to the implant.

In some embodiments, the first elongate member and the second elongate member collectively define a planar Y-shape. In some embodiments, the first portion of the implant is configured to cover at least partially and be attached to a first lateral wall of the vagina, and the second portion is configured to cover at least partially and be attached to a second lateral wall of the vagina such that the first and second portions extend longitudinally down the first and second lateral walls respectively in a direction parallel to a longitudinal axis of the vagina. In some embodiments, the distal end portion of the first elongate member is configured to be attached to or proximate a sacrum.

In some embodiments, the device includes a suture, and a suturing device configured to fix the implant at bodily locations with the use of the suture. In some embodiments, the device includes a slot between the first portion and the second portion, wherein the slot defines one of a U-shape, V-shape, and rectangular shape formed by removal of a piece of material between the first portion and the second portion of the second elongate member.

In some embodiments, a method for implanting a medical device in a patient's body includes creating a vaginal incision; inserting a Y-shaped implant inside the body transvaginally, the implant including a first elongate member having a distal end portion and a proximal end portion, and a second elongate member including a first portion and a second portion such that the second elongate member extend monolithically from the first elongate member; attaching the first portion and the second portion to lateral portions of a vaginal wall such that the first portion and the second portion extend longitudinally down the lateral portions of the vaginal wall; and attaching a distal end portion of the first elongate member to or proximate a sacrum.

In some embodiments, the vaginal incision is an anterior incision at an anterior vaginal wall. In some embodiments, the incision is a posterior incision at a posterior vaginal wall. In some embodiments, the method includes making a cut in the second elongate member to configure it as the Y-shape implant and separate the first portion and the second portion configured to be attached at separate body locations. In some embodiments, the method includes creating an abdominal incision, and attaching the distal end portion of the first elongate member comprises attaching the distal end portion to the sacrum laprosopically through the abdominal incision.

In some embodiments, attaching the distal end portion of the first elongate member includes attaching the distal end portion to the sacrum trans-vaginally through the vaginal incision. In some embodiments, the method includes suturing the implant at bodily locations with the use of a suturing device. In some embodiments, the method includes tensioning the implant appropriately for the repair of pelvic floor disorder. In some embodiments, the method includes trimming an unwanted portion of the implant after attaching the implant. In some embodiments, the implant is coupled to a dilator and an insertion tool for delivery and placement of the implant and the method includes removing the dilator from the body after delivery of the Y-shaped implant within the body; and removing the insertion tool after delivery and placement of the Y-shaped implant. In some embodiments, the method includes closing the vaginal incision.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device comprising:
    a Y-shaped implant including:
        a first elongate member having a distal end portion and a proximal end portion, the first elongate member having a longitudinal axis; and
        a second elongate member formed monolithically with the first elongate member out of a single and planar strip of material, the second elongate member extending from the proximal end portion of the first elongate member in a direction substantially parallel to the longitudinal axis of the first elongate member, the second elongate member having a first portion and a second portion, each of the first portion and the second portion of the second elongate member including a proximal end portion and a distal end portion, the second elongate member defining a substantially linear slot between the first portion and the second portion;
    a sleeve covering at least a portion of the first elongate member;
    a suture coupling the sleeve to the first elongate member, the suture extending along a portion of the sleeve;
    a dilator including a proximal end portion and a distal end portion, the proximal end portion of the dilator configured to be coupled to the first elongate member, the suture extending through the dilator; and
    an insertion tool including a needle configured to be coupled to the dilator.

2. The medical device of claim 1, wherein the first portion of the implant is configured to cover at least partially and be attached to a first lateral wall of the vagina, and the second portion is configured to cover at least partially and be attached to a second lateral wall of the vagina such that the first and second portions extend longitudinally down the first and second lateral walls respectively in a direction parallel to a longitudinal axis of the vagina.

3. The medical device of claim 1, wherein the distal end portion of the first elongate member is configured to be attached to or proximate a sacrum.

4. The medical device of claim 1, further comprising:
    a suturing device configured to fix the implant at bodily locations with use of the suture.

5. The medical device of claim 1, wherein the substantially linear slot is formed by removal of a piece of material between the first portion and the second portion of the second elongate member.

6. The medical device of claim 1, wherein the sleeve covers an entire portion of the first elongate member.

7. A method for implanting a medical device in a patient's body, the method comprising:
    making a cut into a first end of a first elongate member of an implant by a medical operator to form a first portion and a second portion, the first portion extending substantially parallel to the second portion, the implant having a second elongate member, the second elongate member having a proximal end portion and a distal end portion, the proximal end portion of the second elongate member extending monolithically from a second end of the first elongate member, wherein the first portion, the second portion, and the second elongate member, collectively, define a Y-shaped implant, wherein a sleeve covers at least a portion of the second elongate member, a suture couples the sleeve to the second elongate member, and a dilator is coupled to the second elongate member, the suture extending along a portion of the sleeve and through the dilator;
    coupling a needle of an insertion device to the dilator;
    creating a vaginal incision;
    inserting, using the insertion device, the Y-shaped implant inside the body trans-vaginally;
    attaching the first portion and the second portion to lateral portions of a vaginal wall such that the first portion and the second portion extend longitudinally down the lateral portions of the vaginal wall;
    attaching a distal end portion of the first elongate member to or proximate a sacrum; and
    removing the dilator and the sleeve from the patient's body.

8. The method of claim 7, wherein the vaginal incision is an anterior incision at an anterior vaginal wall.

9. The method of claim 7, wherein the incision is a posterior incision at a posterior vaginal wall.

10. The method of claim 7, further comprising creating an abdominal incision, and attaching the distal end portion of the first elongate member comprises attaching the distal end portion to the sacrum laparoscopically through the abdominal incision.

11. The method of claim 7, wherein attaching the distal end portion of the first elongate member includes attaching the distal end portion to the sacrum trans-vaginally through the vaginal incision.

12. The method of claim 7, further comprising suturing the implant at bodily locations via a suturing device.

13. The method of claim 7, further comprising tensioning the Y-shaped implant appropriately for repairing of a pelvic floor disorder.

14. The method of claim 7, further comprising trimming an unwanted portion of the Y-shaped implant after an attachment of the Y-shaped implant.

* * * * *